United States Patent [19]
Evenson

[11] Patent Number: 5,777,241
[45] Date of Patent: Jul. 7, 1998

[54] METHOD AND APPARATUS FOR SAMPLING AND ANALYSIS OF FURNACE OFF-GASES

[76] Inventor: Euan J. Evenson, 484 Donegal Drive, Burlington, Ontario, Canada, L7L 2M7

[21] Appl. No.: 795,861

[22] Filed: Feb. 6, 1997

[51] Int. Cl.⁶ .................................................. G01N 1/22
[52] U.S. Cl. ................... 73/863.11; 73/863.24; 73/863.25; 73/863.83
[58] Field of Search ................ 73/23.31, 31.07, 73/863.11, 863.12, 863.24, 863.25, 863.23, 863.81–863.83, 863.85, 864.34, 864.73, 864.81

[56] References Cited

U.S. PATENT DOCUMENTS

| | | |
|---|---|---|
| 1,798,032 | 3/1931 | Rice . |
| 2,731,832 | 1/1956 | Johnson . |
| 3,559,491 | 2/1971 | Thoen . |
| 3,680,388 | 8/1972 | Critchley et al. ............ 73/863.11 |
| 3,759,087 | 9/1973 | Iwao et al. . |
| 3,766,715 | 10/1973 | Archer . |
| 3,938,390 | 2/1976 | Grey . |
| 4,032,308 | 6/1977 | Lawson et al. . |
| 4,100,806 | 7/1978 | Carbonnelle et al. . |
| 4,161,883 | 7/1979 | Laird et al. . |
| 4,259,867 | 4/1981 | Foundos et al. ............ 73/863.12 |
| 4,283,947 | 8/1981 | George et al. . |
| 4,379,412 | 4/1983 | Wood . |
| 4,485,684 | 12/1984 | Weber et al. ............... 73/863.24 |
| 4,756,200 | 7/1988 | Ramsner et al. . |
| 4,772,454 | 9/1988 | Jarolics . |
| 4,779,466 | 10/1988 | Ramsner et al. . |
| 4,974,455 | 12/1990 | McGowan et al. . |
| 5,039,322 | 8/1991 | Holzl . |
| 5,063,789 | 11/1991 | Tuthill ........................ 73/863.23 |
| 5,166,950 | 11/1992 | Jouvaud et al. . |
| 5,178,022 | 1/1993 | Tomlin . |
| 5,423,228 | 6/1995 | Budd et al. . |
| 5,493,923 | 2/1996 | Balfanz et al. . |

OTHER PUBLICATIONS

Industrial Practice of a New Injection Process of L'air Liquide for Post–Combustion at Vallourec Saint–Saulve by P. Boussard et al., 1992.

New Tools for Improved Operation of High–Efficiency Electric Arc Furnaces by Monika Aderup et al., 1992.

Primary Examiner—Robert Raevis
Attorney, Agent, or Firm—Riches, McKenzie & Herbert

[57] ABSTRACT

A furnace system includes a furnace and a furnace monitoring and control system having a gas analyzer for analyzing the composition of furnace off-gases, and a sampling tube or probe used to obtain a high temperature off-gas sample for delivery to the gas analyzer. Gas samples are drawn to the gas analyzer, via the probe, by a vacuum. The probe is formed as a generally cylindrical or polygonally shaped hollow tube, which when mounted in the system defines a generally vertically extending elongated gas passage along which sample gas is drawn, and whereby sample gas flow in the passage is in a generally vertical direction. The probe is provided with upper and lower openings which extend into the gas passage. The lower opening is provided in gaseous communication with the furnace off-gas stream and is formed so as to permit the substantially unhindered movement of particulate matter, such as dust, downwardly along the gas passage and outwardly through the open bottom end. The upper opening is provided in gaseous communication with the gas analyzer, and a filter is removably positioned across the upper opening to prevent dust and other particulate matter entrained in the sample off-gas from moving through the upper opening and into the gas analyzer. To cool the sample gas and prolong the filter life, part of the probe is provided with a double sidewall construction so as to define a partitioned annular chamber extending about at least part of the gas passage along which cooling fluid may move.

21 Claims, 6 Drawing Sheets

METHOD AND APPARATUS FOR SAMPLING AND ANALYSIS OF FURNACE OFF-GASES

SCOPE OF THE INVENTION

The present invention relates to a method and an apparatus for the sampling and analysis of high temperature furnace off-gases, and more particularly, to an apparatus which includes a gas sampling probe used to continuously obtain gas samples to permit continuous furnace monitoring and control, and a method of using such a probe in conjunction with a furnace monitoring and control system.

BACKGROUND OF THE INVENTION

In the recycling of scrap steel in electric arc furnaces, carbon and oxygen are injected into the furnace to enhance combustion. As a result of inefficient furnace operation, however, combustible hydrogen and carbon monoxide gases are frequently vented as components of the off-gases from the furnace, resulting in a loss of furnace operating efficiency and increasing the costs of steel recovery.

Several attempts have been made to monitor and analyze the constituent elements of furnace off-gases with a view to controlling furnace operations, so as to maximize furnace efficiency. Heretofore, off-gas sampling and analysis has been performed by periodically drawing a gas sample from a hollow tube or probe which is extended into the off-gas stream to a gas analyzer. The probe has an opening in one of its ends which opens to the off-gas stream, and another portion provided in gaseous communication with the gas analyzer by means of a gas line or conduit. Suction is used to draw a gas sample into and along the tube and to the gas analyzer via the gas line. Typically, during sample gas collection, the tube is extended through a side of a vent duct or stack leading from the furnace along which the off-gas moves. In this position, the tube is arranged in a generally horizontal orientation whereby off-gas samples which are drawn flow in a generally horizontal direction along the inside of the tube. While conventional sampling apparatus may be effective in obtaining a single gas sample every few hours, heretofore sampling apparatus have proven ineffective in the continuous collection of samples of furnace off-gases, as they become clogged after extended periods of use.

Dust and other particulate matter from the furnace, and which is entrained in the off-gases, tends to accumulate in the sampling tube and gas lines used to draw the gas sample to the gas analyzer. The clogging of sampling tubes is compounded in conventional gas sampling apparatus in which the sample gas is drawn horizontally. Because of the horizontal orientation of the gas passage, furnace dust tends to accumulate along the inside of the sample tube as the dust settles on the lower surface of the tube. The accumulating dust in turn prevents the effective sampling of the furnace off-gases. The difficulties of accumulating dust and particulate matter are especially acute where the unfiltered sample gas is drawn through sampling tubes which have longer horizontal sample gas passages.

To minimize clogging, it is known to provide a flow of pressurized backflow gas along the probe or tube, to dislodge any accumulated dust and the like. In an attempt to maximize the effectiveness of backflow cleaning by pressurized gas, some conventional sample tubes are formed having a comparatively short length. The shorter length of conventional sampling tubes, however, results in the collection of sample off-gases from the peripheral edges of the off-gas stream, adjacent the sides of the exhaust duct. If air inlets are provided through the sides of the exhaust duct upstream of the sample tube, as for example, to facilitate off-gas flow and cool the off-gases, off-gas samples collected at the edge of the off-gas flow may be non-representative of the actual off-gas as a result of the mixing of off-gases and air.

If the entrained particulate matter is drawn through the gas lines and into the gas analyzer, the dust and particles may clog or otherwise damage the analyzer equipment. To prevent dust and other such particulate matter from entering the gas analyzer, various particle filters have been proposed within or across parts of the sampling tubes. It has been found, however, that the exceptionally high temperatures of off-gases from high temperature furnaces, which exceed temperatures of 3000° F., tends to degrade the filters after prolonged use, causing the filters to crack and/or crumble. To prolong filter life, conventional gas sampling of high temperature furnace off-gases is, therefore, performed only on a periodic basis.

A further difficulty with conventional sampling tubes exists in that the filters used to filter particulate matter from the off-gases are mounted to the probe, so as to locate within the exhaust duct during gas sampling operation. As such, if the filter fails, it is necessary to remove and disassemble the entire gas sampling probe to change the filter. This, in turn, frequently necessitates the shut down of the entire furnace system, leading to production losses.

The disadvantages of prior art gas sampling and analysis apparatus have thus prevented the substantially continuous sampling of off-gases and the continuous monitoring of furnace operations. The result is that with existing sampling and monitoring apparatus, it has not been possible to actively alter the furnace operating conditions in response to off-gas analysis data, so as to maximize furnace efficiency.

SUMMARY OF THE INVENTION

To at least partially overcome the disadvantages of prior art devices, the present invention provides an apparatus for monitoring and analyzing furnace off-gases, which includes a gas sampling tube or probe which has a vertically extending gas passage along which sampled gas is drawn vertically for insertion into a furnace off-gas stream.

Another object of the invention is to provide an apparatus adapted to continuously sample and monitor off-gases from high temperature furnaces, such as electric arc furnaces, without clogging.

A further object of the invention is to provide a probe for use in sampling high temperature furnace off-gases at temperatures as high as 3000° F., and which incorporates a filter for removing dust and other particulate matter which is entrained in the sampled gas, and which is adapted to withstand the high temperature cycling associated with the start-up and shut down of the furnace.

Another object of the invention is to provide a probe for sampling high temperature off-gases, which defines a gas passage which is open to the off-gas stream at its lowermost end to facilitate backflow cleaning.

Another object of the invention is to provide an apparatus for sampling high temperature furnace off-gases which includes a probe configured to obtain a gas sample from a middle portion of the off-gas stream, and which cools the gas sample prior to drawing the sample through an internally housed filter so as to prolong filter lifespan.

Another object of the invention is to provide a probe as part of an apparatus for sampling and monitoring furnace off-gas which incorporates a filter which may be quickly and easily replaced without requiring the removal or disassembly of the probe, or the shut down of the furnace.

A further object of the invention is to provide a method of operating a high temperature furnace system whereby during the furnace heat, furnace off-gases are continuously sampled and analyzed, and where furnace operating conditions are varied having regard to various components of the off-gas to maximize furnace efficiency.

Another object of the invention is to provide a method and an apparatus for operating a furnace by continuously sampling and analyzing furnace off-gases to provide off-gas content and/or temperature data, comparing the sample data with stored data representative of a normalized furnace heat profile and/or previous heat profiles and/or a preferred furnace heat profile, and controlling the furnace operating conditions to compensate for differences between the sample data and the stored data.

In one embodiment, a furnace and a furnace monitoring and control system are provided in which the monitoring and control system includes a gas analyzer for analyzing the composition of furnace off-gases, and a sampling tube or probe used to obtain an off-gas sample from the furnace off-gas stream for delivery to the gas analyzer. Gas samples are drawn to the gas analyzer, via the probe, by a vacuum pump provided either as part of, or in gaseous communication with, the gas analyzer. The probe may be used to sample off-gases from a number of different furnace operations and/or reaction vessels, but is most suitably used to sample high temperature off-gases from electric arc furnaces, wherein the off-gas temperature may be as high as 3000° F.

The probe is formed as a generally cylindrical or polygonally shaped hollow tube, which defines a generally vertically extending elongated gas passage. The probe is provided with upper and lower openings which extend into the elongated gas passage. The lower opening is provided in gaseous communication with the furnace off-gas stream and the upper opening is provided in gaseous communication with the gas analyzer by a gas conduit tube. In use, sample gas is drawn into the probe through the lower opening, and the sample gas flows in the passage in a generally vertical direction to the upper opening where it passes out of the probe. Preferably, the gas passage is open to the off-gas stream at its bottom end to define the lower opening into which sample off-gases are drawn. More preferably, the open bottom end further is formed to permit substantially unhindered movement of particulate matter, such as dust, downwardly along the vertical sides of the gas passage and outwardly therefrom through the open bottom end.

The probe is mounted through the wall of an off-gas exhaust duct used to vent the off-gases from the furnace. The probe is positioned so that the gas passage remains in a generally vertical orientation and the bottom end of the probe locates in a central area of the off-gas stream. In this position, sample off-gas is drawn from the middle area of the off-gas stream through the bottom end into and vertically along the passage to the upper opening. At the upper end of the probe the drawn sample gas moves through the upper opening and to the gas analyzer via the conduit tube.

A filter may be positioned across the upper opening to prevent dust and other particulate matter entrained in the sample off-gas from passing through the upper opening and into the gas analyzer. While numerous types of filters are possible, including natural stone and ceramic filters, the filter is preferably formed from either a high temperature fibre based filter or porous silicon carbide, both of which have been found to provide enhanced resistance to thermal degradation on prolonged contact with high temperature off-gases.

The filter may be removably secured across the upper opening of the probe, as for example, by means of screws, a locking ring, complementary threaded couplings on the filter and about the opening or by other types of fastening members. Preferably, the filter has an elongated cylindrical shape having a diameter less than that of the upper opening. The filter may thus be secured in place by a threaded coupling which permits the removal and replacement of the filter through the upper opening, without requiring the removal of the probe from the off-gas exhaust duct.

The monitoring and control system may further include a backflow gas source provided selectively in gaseous communication with the gas passage to provide pressurized gas flow downwardly along the gas passage to dislodge any particulate matter which accumulates therein. By selectively providing the backflow gas source in gaseous communication with the gas passage, backflow gas may be directed through a vent port leading directly into an upper portion of the gas passage and/or through the upper opening and filter to backflow purge accumulated dust from the surface of the filter.

To reduce the effects of thermal degradation on the filter, and partially arrest ongoing chemical reactions occurring within the sampled high temperature off-gases, the probe preferably also includes cooling apparatus used to lower the temperature of the sample gas as it moves upwardly in the gas passage towards the filter. In the simplest embodiment, part of the probe is provided with a double sidewall construction having an inner sidewall and a radially spaced outer sidewall. The sidewalls are joined by annular lower and upper end walls and define an annular chamber extending about at least part of the gas passage. Two or more partition members extend across the annular chamber and divide the chamber into a series of connecting coolant channels.

Coolant fluid, such as water or glycol solutions, may be pumped through the coolant channels to cool the collected sample gas as it is drawn upwardly along the gas passage. Coolant fluid is pumped through the coolant channels at a rate of between 5 and 100 gallons per minute, and more preferably, at a rate of between about 40 and 80 gallons per minute.

The conduit tube may be made of a number of materials, including metals, rubber, plastics, or where cooled gases are to be analyzed, even Teflon to prevent chemical reactions between the sample off-gas and the gas conduit tube as the gas sample moves through the tube.

Preferably, the gas analyzer is electronically linked to a furnace control unit, such as a microprocessor or central processing unit (CPU) which controls furnace operations. In response to data input from the gas analyzer, the furnace control unit may thus be used to change furnace operating conditions, such as carbon or oxygen content, combustible gas content (including hydrogen and carbon monoxide gases), and/or overall furnace temperature to achieve maximum furnace efficiency. More preferably, the gas analyzer and/or CPU includes data storage capability for storing sample gas analysis data from a number of separate furnace heats, and/or a normalized furnace heat and/or data representing an optimum furnace heat. The gas analyzer is therefore used to continuously monitor off-gas samples and prepare an ongoing furnace heat profile of various off-gas constituents. Off-gas constituents which can be profiled, include carbon monoxide content, oxygen content, hydrogen content, carbon dioxide content and/or furnace or off-gas temperatures. During the furnace operation, individual heat profiles may thus be continuously compared with profiles representative of average or preferred furnace heats, and the furnace operating conditions may be varied to improve furnace efficiency.

Accordingly, in one aspect the present invention resides in an apparatus for sampling high temperature furnace off-gases from an off-gas stream and for delivering sample gas substantially free of particulate matter to gas analyzer means, the apparatus including,

- an elongated sampling probe, gas conduit means providing gaseous communication between said probe and said gas analyzer means and means for drawing said sample gas to said gas analyzer via said conduit means, the sampling probe including,
- an inner sidewall substantially defining an elongated, vertically extending sample gas passage, said passage open to the stream at a lowermost open end,
- an upper opening spaced above said open end and permitting gas flow between said passage and said conduit means,
- an outer sidewall spaced radially outwardly about at least part of said inner sidewall and defining a generally annular chamber therebetween,
- upper chamber wall means extending radially from said inner sidewall to said outer sidewall,
- lower chamber wall means extending radially from said inner sidewall to said outer sidewall,
- first and second partition means, each extending across said annular chamber between said inner sidewall and said outer sidewall, and being spaced from said lower wall means to divide the annular chamber into at least two fluid communicating coolant fluid channels for cooling said sample gas in said passage,
- means for introducing coolant fluid into said coolant fluid channels,
- filter means disposed across said upper opening for filtering particulate matter from said sample gas as said sample gas is drawn through said upper opening, the lowermost open end substantially unobstructing downward movement of said particulate matter filtered from said sample gas, outwardly from said gas passage.

Accordingly, in another aspect the present invention resides in an apparatus for obtaining a high temperature gas sample from an electric arc furnace off-gas stream and for delivering said sample to a gas analyzer, the apparatus comprising,

- a hollow sampling probe defining a vertically oriented elongated cylindrical sample gas passage, said passage opening downwardly at its lowermost end into a bottom opening of said off-gas stream, said probe including an upper opening through which said sample gas moves from said gas passage to the gas analyzer,
- vacuum means in gaseous communication with said upper opening for drawing said sample from said off-gas stream into said passage via said bottom end opening and outwardly from said passage through said upper opening to said gas analyzer,
- filter means provided across said upper opening for filtering particulate matter from said sample as said sample is drawn through said upper opening.

In a further aspect, the present invention resides in the use of an apparatus for sampling and analyzing high temperature furnace off-gases from an off-gas stream and for controlling furnace operations in response to the sample analysis, the apparatus comprising,

- gas analyzer means for analyzing said sample gas, an elongated sampling probe, and gas conduit means providing gaseous communication between said probe and said gas analyzer means and means for drawing said sample gas to said gas analyzer via said conduit means,
- the sampling probe comprising,
- an inner sidewall substantially defining an elongated sample gas passage, said passage open to the stream at a lowermost open end,
- an upper opening spaced above said open end and permitting gas flow between said passage and said conduit means,
- an outer sidewall spaced radially outwardly about at least part of said inner sidewall and defining a generally annular chamber therebetween,
- upper chamber wall means extending radially from said inner sidewall to said outer sidewall,
- lower chamber wall means extending radially from said inner sidewall to said outer sidewall,
- first and second partition means, each extending across said annular chamber between said inner sidewall and said outer sidewall, and being spaced from said lower wall means to divide the annular chamber into at least two fluid communicating coolant fluid channels for cooling said sample gas in said passage,
- means for introducing coolant fluid into said coolant fluid channels,
- filter means disposed across said upper opening for filtering particulate matter from said sample gas as said sample gas is drawn through said upper opening,
- wherein the lowermost open end substantially unobstructs downward movement of said particulate matter filtered from said sample gas, outwardly from said gas passage, and
- backflow gas supply means selectively operable to supply backflow gas flow downwardly along said gas passage, wherein sampling of said off-gas is performed by the steps of:

(a) activating said means for drawing a sample to said gas analyzer via said gas passage to draw an off-gas gas sample into said gas passage via the lowermost open end, (b) simultaneously while drawing said sample, circulating coolant fluid through said coolant channels to cool said sample as its moves along the passage, and (c) periodically interrupting the drawing of said off-gas sample and activating said backflow gas supply means to provide backflow gas along said gas passage to assist in dislodging particulate matter therein.

BRIEF DESCRIPTION OF THE DRAWINGS

Further objects and advantages of the invention will appear from the following description, taken together with the accompanying drawings in which.

DETAIL DESCRIPTION OF THE DRAWINGS

Figure 1:
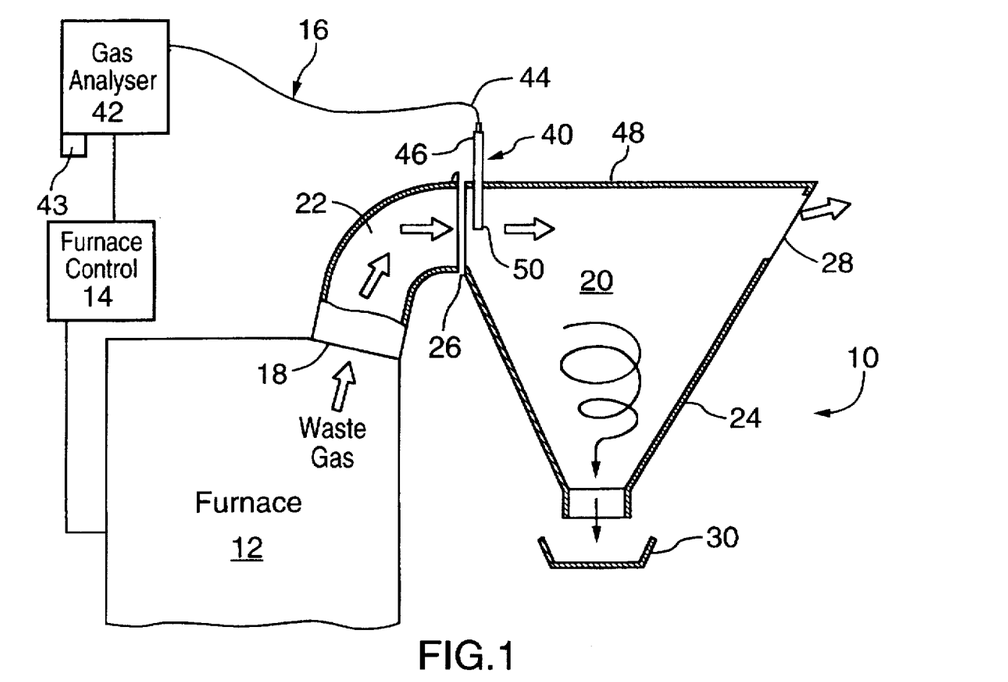
FIG. 1 is a schematic view of a furnace and an off-gas sampling and analysis apparatus in accordance with the present invention.

Reference is made first to FIG. 1 which shows a system 10 used in the reclamation of scrap steel. The system 10 includes an electric arc furnace 12, a furnace controlling central processing unit (CPU) 14 used to control various furnace operating conditions, and a furnace off-gas sampling and analysis assembly 16. As will be described, off-gas sampling and analysis assembly 16 is used continuously during the furnace heat to obtain and analyze furnace off-gas constituents, and provide data respecting the various off-gas constituents to the CPU 14.

The furnace 12 uses electricity either by itself, or in conjunction with supplemental natural gas burners, and injected oxygen to make steel or other ferrous or non-ferrous products. In a conventional manner, furnace operating conditions are varied by the activation of the natural gas burners to increase the furnace temperature, as well as by the selective additional combustion enhancing additives, such as carbon and/or oxygen, and/or combustible hydrogen and carbon monoxide gases.

Off-gases from the furnace 12 are vented outwardly through an opening 18 in the top of the furnace 12, and then into an exhaust duct 20 via an elbow 22. The elbow 22 is provided to change the direction of flow of the off-gas stream from a generally vertical flow when the off-gases move through the opening 18, to a generally horizontal flow, as the off-gases move into and through the exhaust duct 20. The exhaust duct 20 opens downwardly into a dust collection hopper portion 24 which is used to collect particulate matter, such as furnace dust, which is carried from the furnace 12 entrained by the off-gases.

FIG. 1 shows best the exhaust duct 20 as being separated from the elbow 22 by a gap 26 approximately 2 to 8 inches wide. The gap 26 advantageously permits air to be drawn into the duct 20. Air drawn through the gap 26 mixes with the off-gas stream to facilitate off-gas cooling, and slows the flow of off-gas as it moves horizontally over the hopper portion 24 and towards an exhaust fume outlet 28. As a result of the slowed off-gas flow, entrained particulate matter falls from the off-gas stream into the hopper portion 24 where it is collected in a bin 30.

Figure 2:
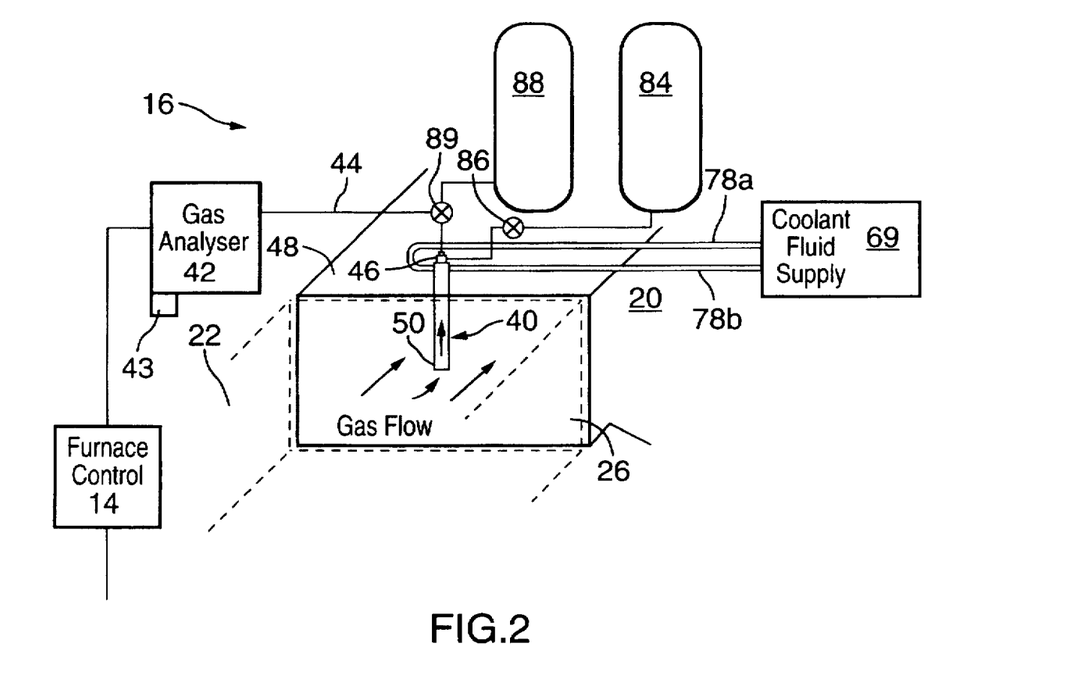
FIG. 2 is a schematic view of a gas sampling probe for use in the off-gas sampling and analysis apparatus of FIG. 1, showing its position in a furnace off-gas exhaust duct.

FIG. 2 shows best the off-gas sampling and analysis assembly 16 as including a metal gas sampling probe 40 and an off-gas analyzer 42 which, during gas sampling, are provided in gaseous communication by a metal gas conduit tube 44. The gas analyzer 42 is provided with an internal vacuum pump 43 which in use, draws the sample gas into the probe 40 and to the analyzer 42 for analysis.

The sampling probe 40 is formed having an elongated generally hollow tube-like structure and is positioned in the exhaust duct 20 in a generally vertical orientation. The probe 40 extends from a top end 46 downwardly through the top panel 48 of the exhaust duct 20 to a lowermost end 50. The probe 40 has an overall length of about 5 feet and extends downwardly so that its lowermost end 50 locates in the middle area of the off-gas stream which flows through the exhaust duct 20.

Figure 3:
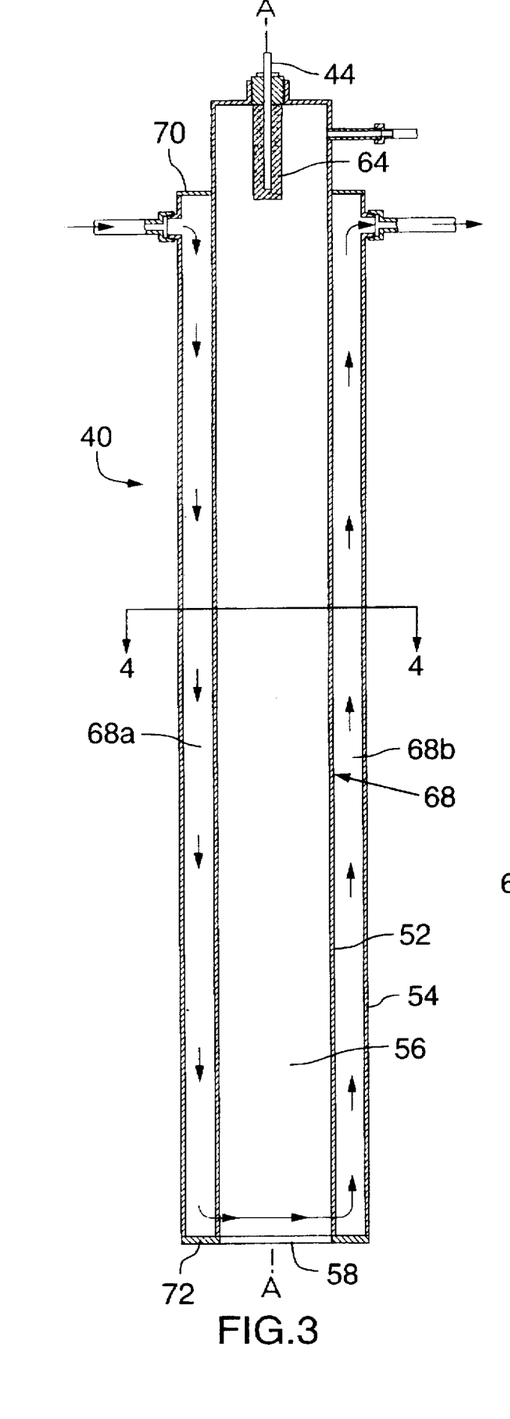
FIG. 3 shows a cross-sectional view of the probe shown in FIG. 2.
Figure 4:
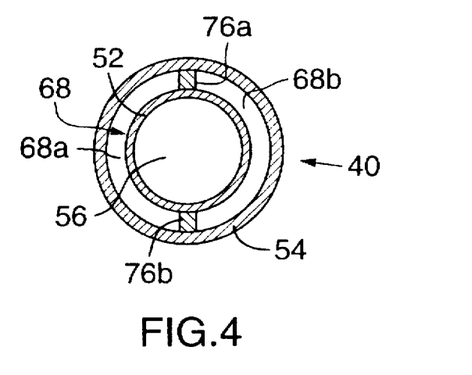
FIG. 4 is a cross-sectional view of the probe shown in FIG. 3, taken along lines 4-4'.
Figure 5:
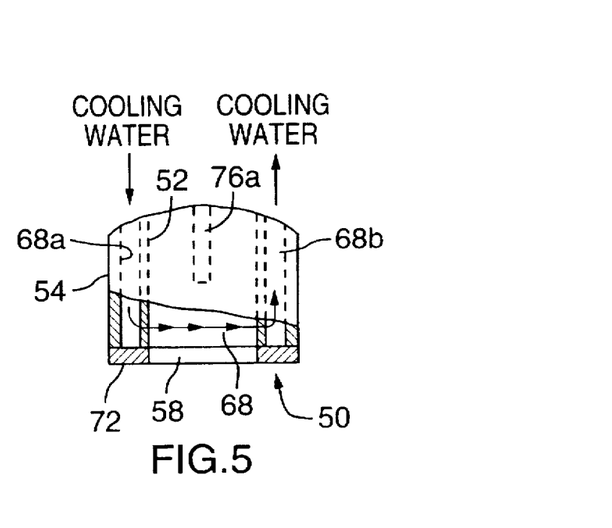
FIG. 5 is an enlarged partially cut-away schematic view of the lowermost bottom end of the probe shown in FIG. 3.

As shown best in FIGS. 3 to 5, the probe 40 has a double sidewall construction and includes a stainless steel cylindrical inner sidewall 52 and a stainless steel cylindrical outer sidewall 54 provided concentrically about the inner sidewall 52, and an internally housed filter 64. The inner sidewall 52 extends the length of the probe 40 and defines an elongated, vertically extending cylindrical gas passage 56 which, when the probe 40 is inserted in the duct 20, is centred on a vertical axis A—A (FIG. 3). The gas passage 56 has smooth vertical sides, and a radial diameter of between about 1 and 3 inches. The passage 56 is open to the off-gas stream at its lowermost end through a bottom opening 58 which is defined by the lowermost extent of the cylindrical inner sidewall 52. It is, to be appreciated that because the bottom opening 58 is also defined by the sidewall 52, dust and other particulate matter in the gas passage 56 may fall from the probe 40, unobstructed by either the sidewall 52 or the bottom opening 58.

Although not essential, the outer sidewall 54 is shown slightly shorter than the inner sidewall 52, extending from the lowermost end 50 of the probe 40 to a position approximately 6 inches below the top end 46. The outer sidewall 54 has a radial diameter of between about 2 and 4 inches and is spaced radially outwardly from the inner sidewall 52, so as to define an annular chamber 68 therebetween. An annular upper end wall 70 (FIG. 6) extends radially outwardly from the inner sidewall 52 to the outer sidewall 54 to close an uppermost end of the chamber 68. The lower end of the chamber 68 is similarly closed by an annular lower end wall 72 (FIG. 5) which extends radially outwardly from the lowermost end of inner sidewall 52 to the outer sidewall 54.

As seen in FIGS. 4 and 5, a pair of elongate dividing webs 76a,76b extend from the inner sidewall 52 across the chamber 68 to join with the outer sidewall 56. The uppermost edge of the dividing webs 76a,76b are provided in sealing contact with the upper end wall 70. The webs 76a,76b extend downwardly from the end wall 70 to a position spaced approximately 3 inches above the lower end wall 72 (FIG. 5). In this manner, the webs 76a,76b divide the chamber 68 into two communicating coolant fluid channels 68a,68b.

Figure 6:
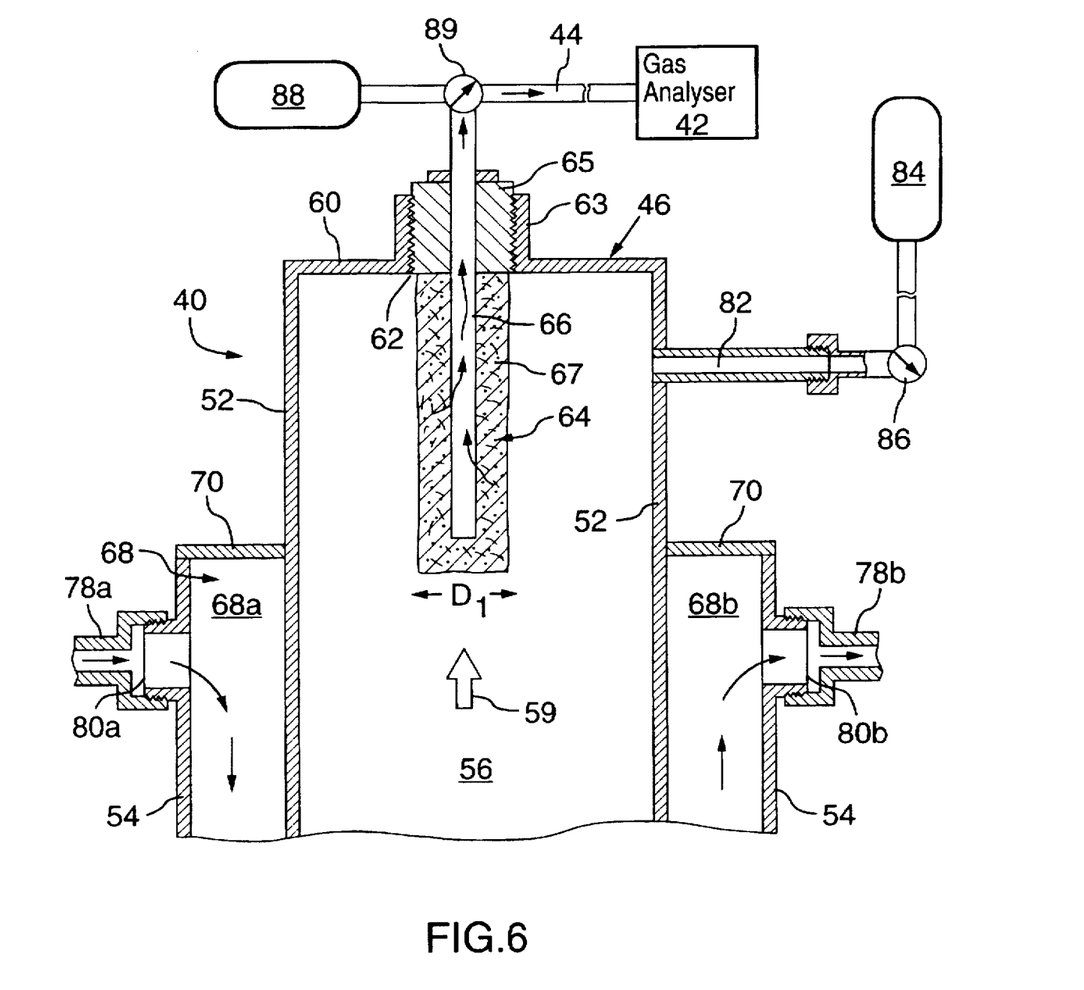
FIG. 6 is an enlarged schematic view of the uppermost end of the probe shown in FIG. 3, showing sample gas flow during off-gas sample collection and analysis.

FIG. 6 shows best the probe 40 as further including coolant fluid ports 80a,80b formed through outer sidewall 54 and providing fluid communication therethrough with the coolant fluid channels 68a,68b, respectively. The ports 80a, 80b are spaced toward the chamber upper end wall 70. Coolant fluid such as water is pumped from a coolant fluid supply 69 (FIG. 2), via inflow hose 78a, through the port 80a and into fluid channel 68a. As the coolant fluid is pumped into the chamber 68, the fluid flows first downwardly along fluid, coolant channel 68a to the bottom of the webs 76a, 76b, then into and upwardly along coolant channel 68b, and outwardly from the chamber 68 via the port 80b. After moving out of the chamber 68, the coolant fluid moves via outflow hose 78b, to the supply 69, where it is chilled prior to recirculation back through the coolant channels 68a,68b.

Figure 7:
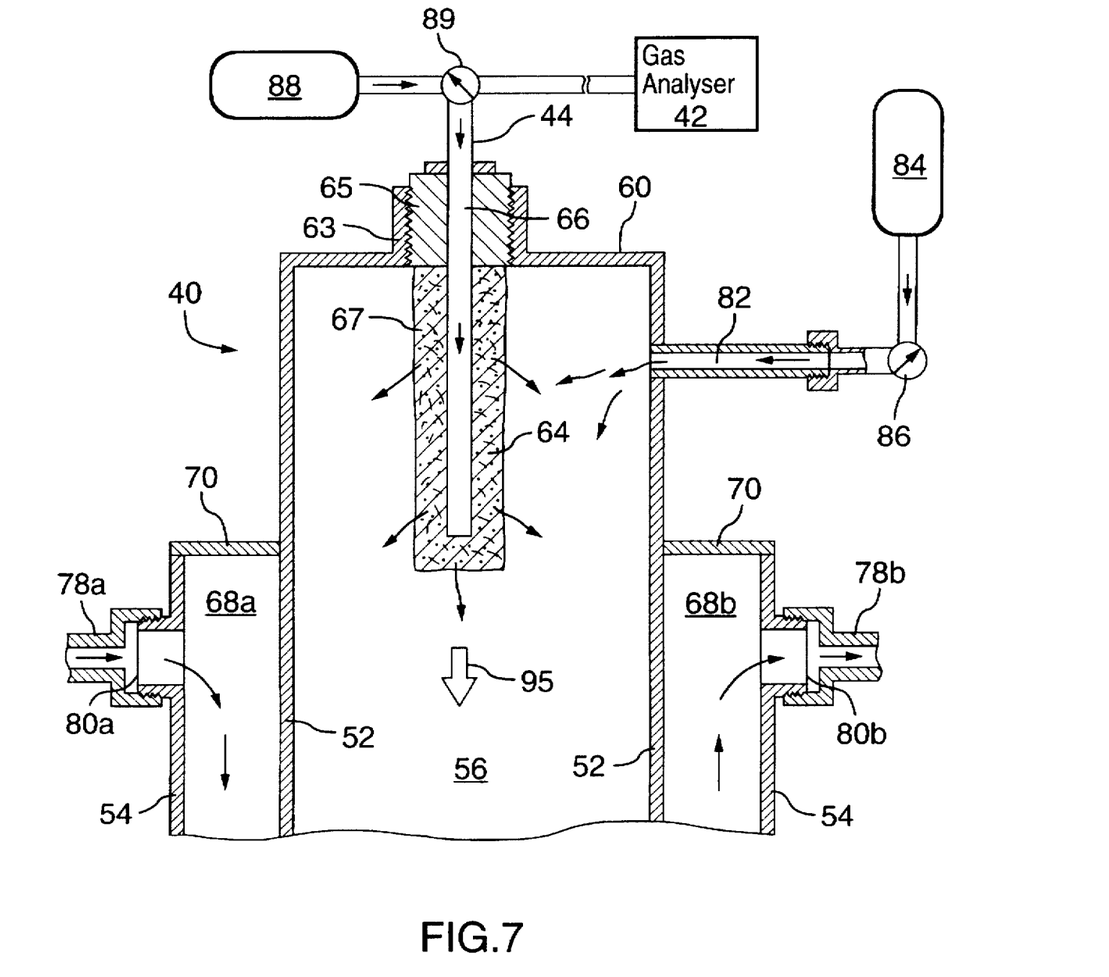
FIG. 7 is an enlarged schematic view of the uppermost end of the probe shown in FIG. 3, showing backflow gas flow during backflow cleaning of the probe.

FIGS. 6 and 7 show best the uppermost end of the gas passage 56 as being closed by a top wall 60. A circular upper opening 62 having a diameter of about 1 inch is formed through the top wall 60 centred on the axis A—A. An internally threaded rim 63 extends upwardly from the top wall 60 about the opening 62 for use in removably coupling the filter 64 in the probe 40.

The filter 64 includes an externally threaded steel end 65 which has a complementary size and threading to the rim 63, and a filter tip 67 which is cemented to the end 65 by a thermally stable cement. FIGS. 6 and 7 show best the filter tip 67 as comprising a generally cylindrical and elongated porous silicon carbide filter. The tip 64 has a 10 micron porosity, and a diameter $D_1$ of approximately 22 millimeters, so as to fit through the upper opening 62. The filter tip 67 has a length of about 6 inches and when the filter 64 is coupled to the rim 63, the tip 67 extends downwardly from a threaded end 65 aligned with the axis A—A. An axially aligned bore 66 having a diameter of between about 0.5 and 1.5 cm, extends downwardly through the end 65 and along the centre of the filter 64 to a position approximately 1 cm from the lowermost end of the filter tip 67. In this manner, the filter 64 may be positioned across the upper opening 62 by lowering the tip 67 through the opening 62 and turning the filter 64 to couple the end 65 to the rim 63.

The filter 64 is replaceably coupled in position in the upper opening 62 by the complementary threaded engagement of the end 65 with the threaded rim 63. The threaded coupling of the filter 64 to the top wall 60, combined with filter diameter $D_1$ being less than that of the opening 62, advantageously permits the simplified replacement of the filter 64 in the event it should fail or become clogged after prolonged use. Because the filter 64 is configured to pass through the opening 62, the filter 64 may be removed or inserted through the top end 46 of the probe 40, without requiring the time consuming removal of the probe 40 from the exhaust duct 20 or even the shut down of the furnace 12.

An inlet end of the gas conduit tube 44 is coupled over the bore 66 which extends through the filter end 65. In this manner, off-gas samples drawn from the gas passage 56, through the filter 64 move along the bore 66 through the upper opening 62, and into the conduit tube 44.

FIGS. 6 and 7 show the probe 40 as further including a vent duct 82 spaced towards the top end 46 of the probe 40, and a first source of pressurized backflow gas 84. The vent duct 82 extends through the inner sidewall 52 adjacent the filter 64. The vent duct 82 is selectively provided in gaseous communication with the backflow gas source 84 by the operation of a valve 86. The valve 86 may be operated to either prevent or permit gaseous communication between the gas source 84 and vent duct 82. The backflow gas source 84 is at a gas pressure higher than the gas pressure in the gas passage 56, whereby gaseous communication between the duct 82 and gas source 84 causes pressurized gas to backflow from the gas source 84 into the passage 56, downwardly along the probe 40, and out through opening 58.

FIGS. 2, 6 and 7 show best the system 10 as further including a second pressurized backflow gas source 88 and a second conduit valve 89. The second backflow gas source 88 is also at a pressure higher than the gas pressure in the gas passage 56. The conduit valve 89 is selectively operable to either permit sample gas flow along the conduit tube 44 between the upper opening 62 and the gas analyzer 42, or to provide gaseous communication between the upper opening 62 and the second backflow gas source 88. By the conduit valve 89 connecting the gas source 88 to the upper opening 62, pressurized gas backflows through the opening 62 and filter 64 and downwardly along the gas passage 52.

In operation of the furnace system 10, the furnace 12 is charged with steel (or other material) to be made, and the CPU 14 is used to initialize the furnace heat. Simultaneously with the furnace 12 start up, the off-gas sampling and analysis assembly 16 is activated to begin monitoring of the furnace off-gases.

Upon the activation of the system 10, the coolant fluid supply 69 is activated to pump cooling water through the coolant channels 68a,68b of the probe 40. To ensure sufficient cooling of high temperature off-gases, it is preferred that cooling water is pumped through the fluid coolant channels 68a,68b at a rate of between approximately 5 to 100 gallons per minute, and more preferably, between about 40 to 80 gallons per minute.

To sample the furnace off-gases, the valves 86,89 are moved to the positions shown in FIG. 6, whereby valve 86 prevents gaseous communication between the backflow gas source 84 and vent duct 82, and valve 89 is operated to permit gaseous communication between the upper opening 62 and the gas analyzer 42. With the conduit valve 89 connecting the conduit tube 44 to the gas analyzer 42, the vacuum source 43 draws a gas sample from the off-gas stream upwardly into the probe 40 and gas passage 56 via the bottom opening 58. As the sample gas is drawn towards the analyzer 42, it moves vertically along the gas passage 56 in the direction of arrow 59, and is cooled by the movement of the cooling water through the fluid coolant channels 68a,68b. By the time the sample gas reaches the filter 64 at the top end 46 of the probe 40, the sample gas has been cooled to both arrest ongoing chemical reactions within the sampled gas, thereby stabilizing the gas sample for analysis, and to reduce the gas temperature so as to prevent thermal degradation of the silicon carbide filter tip 67. The vacuum pump 43 draws the gas sample through the porous silicon carbide filter tip 67 and into the tube 44 via the bore 66 and upper opening 62. As the sample gas passes through the filter tip 67 and into the bore 66, particulate matter, such as dust, which is entrained in the gas sample, is filtered from the sample and particulate-free gas moves through the tube 44 to the analyzer 42 for analysis.

Off-gas sampling is performed almost continuously during the furnace heat. To prevent dust and other particulate matter from clogging the filter 64 and gas passage 56, backflow gas is periodically flushed through the filter 64 and gas passage 56 to dislodge any accumulated particles. Because the backflow gas source 88 is provided at pressures above the gas pressure in the passage 56, when the conduit valve 89 connects the conduit tube 44 to the gas source 88, backflow gas flows from the source 88 into the passage 56 via the upper opening 62 and filter 64. The backflow of gas through the filter 64 acts to dislodge any particles or debris which have accumulated on the outer surface of the filter tip 67.

Similarly, by operating the valve 86 to provide gaseous communication between the vent duct 82 with the backflow gas source 84, pressurized gas may further backflow into the gas passage 56 via the duct 82 to dislodge any dust or other particulate matter which may accumulate along the inner sidewall 52. In addition, by positioning the vent duct 82 adjacent the filter 64, the operation of the valve 86 to backflow gas through the vent duct 82 advantageously directs a stream of backflow gas directly at the filter 64 to further assist in dislodging accumulated particulate matter thereon.

To avoid contamination of the sample gas in the passage 56 and prevent faulty gas analysis data, it is preferable that each of the backflow gas sources 84,88 comprise a source of pressurized non-reactive gases. Suitable backflow gases would, therefore, include gases such as nitrogen, as well as inert gases including helium, neon, xenon and argon, to name but a few.

The gas backflow through the vent duct 82 may occur simultaneously or independently from gas backflow through the filter 64. Preferably, the valves 86 and 89 are operated alternately in succession to sequentially provide communication with the respective backflow gas sources 84,88 to produce the flow of backflow gas downwardly along the gas passage 54 in the direction of arrow 95 shown in FIG. 7. The provision of separate backflow gas sources 84,88 advantageously permits gas to backflow through the vent duct 82 and filter 64 under different pressures. If desired, however, a single backflow gas source may equally be used, either with or without gas regulator valves to provide different backflow pressures.

It is to be appreciated that because the inner sidewall 52 is formed having a smooth cylindrical wall construction, any dislodged particulate matter falls, both together with the backflow gas and under gravity, downwardly through the bottom opening 58 of the probe 40. The bottom opening 58 has the same radial diameter as inner sidewall 52 so that there is no obstruction to the downward movement of particles from the gas passage 56. Because the bottom opening 58 is configured to permit substantially unhindered movement of dust and other particulate matter from the passage 56 during backflow cleaning, particles and dust will not tend to accumulate about the opening 58, where they may otherwise clog the probe 40 and hinder gas flow.

FIG. 3 shows the passage 56 having parallel sidewalls. It is to be appreciated that the passage sidewalls could also flare outwardly towards the bottom opening 58 and with the diameter of the bottom opening 58 being at least as large as the largest part of the passage 56 to permit the unobstructed vertically downward movement of particles therefrom. As a result of the vertical orientation and smooth sidewalls of the gas passage 56, backflow cleaning of the probe 40 will be assisted by the dislodged particulate matter falling from the passage 56 under gravity. The gas passage 52 construction thus permits the probe 40 to have a comparatively longer length, permitting the collection of gas samples from a mid-portion of the off-gas stream.

During the furnace heat, the probe 40 is operated to substantially continuously obtain gas samples from the off-gas stream. Gas sampling is interrupted only periodically, as for example after a five to sixty minute interval of gas sampling or timed to coincide with inherent process pauses, to backflow gas through the filter 64 and vent duct 82 and purge the probe 40 of any accumulated furnace dust or other particulate matter. Preferably, gas sampling is interrupted to coincide with process pauses in the furnace heat which occur on charging, tapping and the like. In this manner, the gas analyzer 42 continuously analyses the off-gas samples during the furnace heat, and provides ongoing data to the CPU 14 indicative of the off-gas constituents.

The central processing unit 14 controls the furnace environment to improve quality of the recovered steel and reduce explosive gas content. In this regard, during the furnace heat the CPU 14 continuously regulates furnace operating conditions, such as electric current in the furnace, the oxygen and/or carbon monoxide concentrations, carbon content and the furnace temperature, as for example, by the activation and deactivation of supplemental gas burners and/or electric current flow.

The CPU includes storage memory for storing control data representing off-gas profiles of one or more previous furnace heats, and/or data representative of a preferred efficiency furnace heat. The CPU 14 also includes software for compiling an ongoing profile of various off-gas components as the furnace heat progresses, and for comparing the data supplied from the gas analyzer 42 with the stored control data. The gas analyzer 42 is electronically linked to the central processing unit 14, whereby sample gas analysis data from the gas analyzer 42 is electronically sent to the CPU 14. Over the course of the furnace heat, the gas analyzer 42 continuously monitors and profiles sample off-gas content with respect to one or more of temperature, carbon monoxide concentration, hydrogen gas concentration, carbon dioxide concentration and oxygen concentration. The data from the gas analyzer 42 which is electronically transmitted to the CPU 14 is continuously compared against control data. Where variances occur between the data received from the gas analyzer 42 and control data stored in the CPU 14, the CPU 14 provides control signals to the furnace 12, adjusting the furnace operating conditions so as to maximize combustion efficiency.

Figure 8:
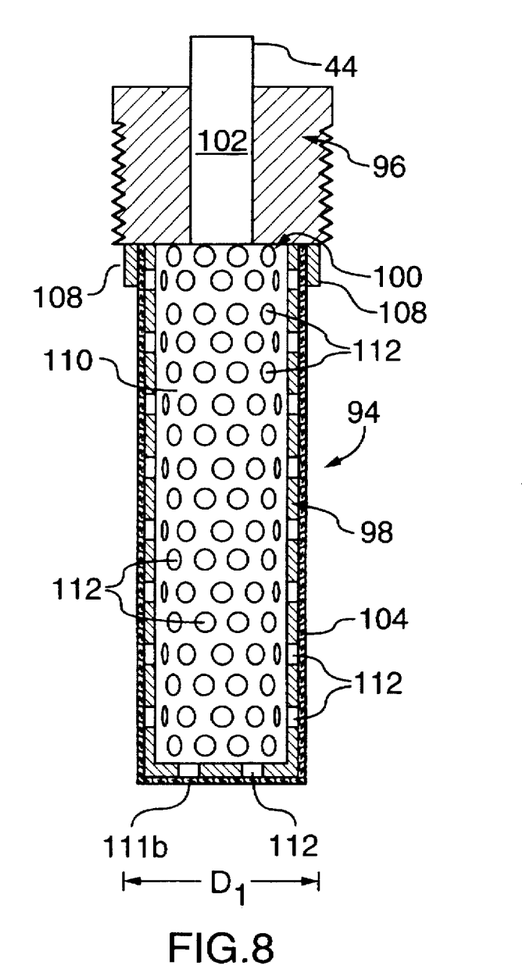
FIG. 8 is a cross-sectional view of a filter for use in the probe of FIG. 2 in accordance with a further embodiment of the invention.
Figure 9:
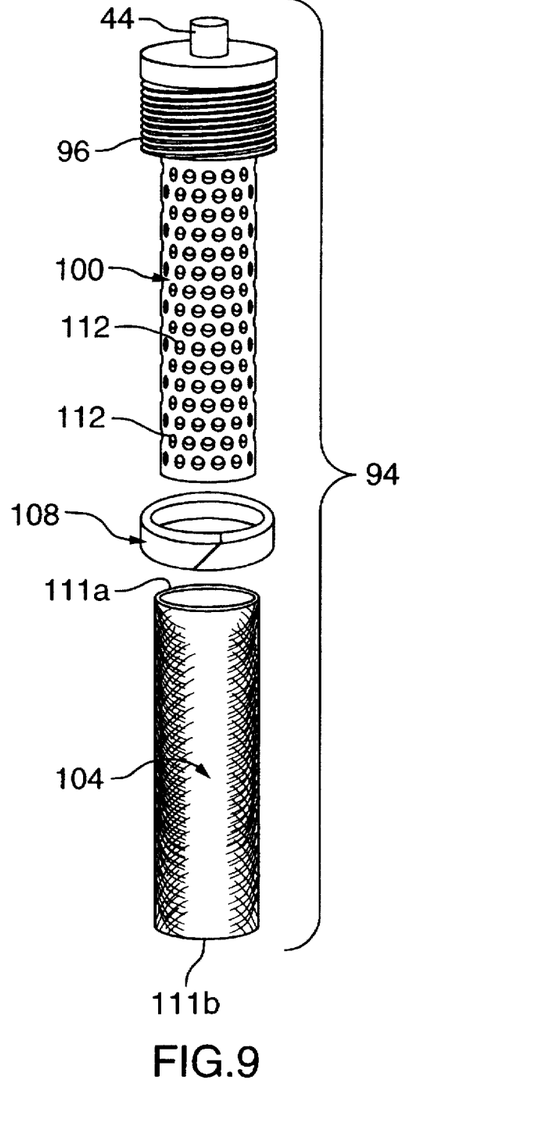
FIG. 9 is an exploded view illustrating the assembly of the filter shown in FIG. 8.

While FIGS. 3, 6, and 7 describe the use of a silicon carbide filter 64 as being threadedly coupled to the rim 63, other filter configurations are also possible and will become apparent. FIGS. 8 and 9 show an alternate filter 94 for use in the probe 40 in accordance with a further embodiment of the invention.

Like the silicon carbide filter 64, the filter 94 includes a threaded steel end 96 which has a complementary size and threading to the rim 63 (FIG. 6), and an elongated generally cylindrical filter body 98. The filter body 98 has a maximum diameter $D_1$ selected so as to permit its insertion downwardly through the probe opening 62 in the same manner as the silicon carbide filter 64. FIG. 9 shows best the filter body 98 as comprising three parts: a perforated stainless steel cylindrical support 100; a high temperature fibre sleeve 104; and a stainless steel split-ring 108.

The cylindrical support 100 is welded to the threaded steel end 96. The support 100 has a hollow interior 110 in gaseous communication with a bore 102 formed axially through the threaded end 96, and which in turn connects to gas conduit tube 44. A plurality of apertures 112 are formed through the support to permit substantially unhindered gas flow into and from the support interior 110.

The high temperature fibre sleeve 104 has an open top end 111a and closed bottom end 111b and is configured to snugly fit over the support 100. The fibre sleeve 104 is made of high temperature fibre based material such as Nomex, or other ceramic based fibres. The sleeve 104 has a pore size of between about 0.1 to 25 microns, and preferably about 1 micron during gas sampling operations. The applicant has, however, discovered that on backflow purging of filter 94, the sleeve 104 advantageously inflates partially like a balloon. The inflation of the sleeve 104 causes the fibre material to stretch with the result that the pore size of the sleeve 104 increases by up to about 25%. The increased pore size of the sleeve 104 on purging advantageously facilitates the dislodging of any particles which collect on the filter body 98 during gas sampling.

The stainless steel split-ring 108 is formed so that the ring ends are resiliently deformable from an undeformed position to a deformed position. When undeformed, the ring 108 has a diameter slightly less than diameter $D_1$. In the deformed position, the ends of the split-ring 108 are spaced apart whereby the splitring 108 may be slid over the sleeve 104 and support 100 to the position adjacent the end 96 shown in FIG. 8. By releasing the ends of the split-ring 108, the ring 108 resiliently returns to its undeformed configuration, firmly clamping the fibre sleeve 104 against the support 100.

Figure 10:
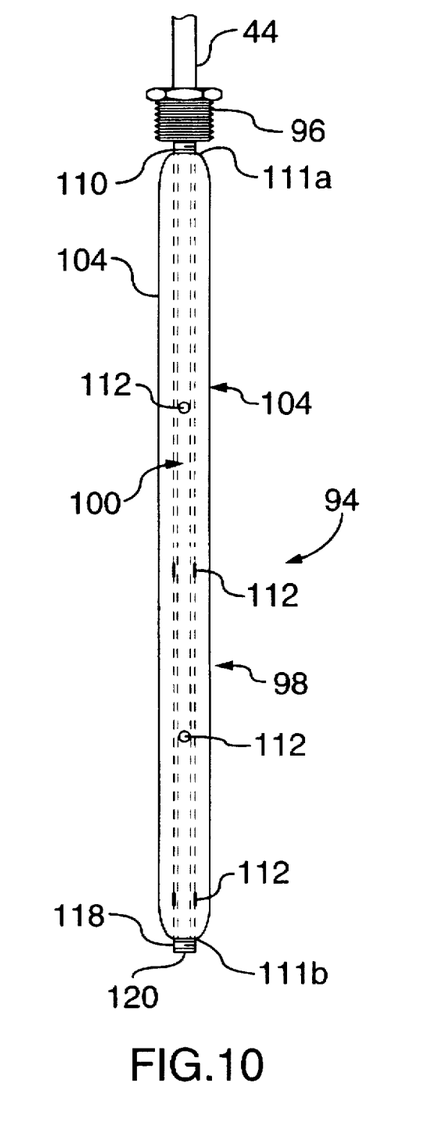
FIG. 10 is a schematic view of an alternate embodiment of a filter for use with the present invention.

It is to be appreciated that while FIGS. 8 and 9 describe the use of a split-ring 108 to clamp the sleeve 104 in place on the support 100, other clamping structures mechanisms are also possible including, for example, hose clamps, solid metal rings, and wire wrap. FIG. 10 shows one modified version of the filter 94 shown in FIGS. 8 and 9, wherein like reference numerals are used to identify like components.

The filter 94 of FIG. 10 includes a stainless steel end 96 and a filter body 98. The filter body 98 has an overall length of about 16 inches and comprises a perforated hollow cylindrical support 100, which is closed at its bottom end by a seal 120, and a high temperature fibre sleeve 104. As shown in FIG. 10, the sleeve 104 has a diameter larger than that of the support 100, and fits loosely thereover during gas sampling.

The sleeve 104 is open at both its upper and lower ends 111a,111b for simplified manufacture. The ends 111a,111b are clamped in a sealed arrangement to the support 100 by upper and lower wire wraps 116,118.

While the use of a sampling probe 40, having a cylindrical inner sidewall 52 is shown in the preferred embodiments of the invention, the invention is not so limited. It is to be appreciated that probe 40 having polygonal or irregular shaped or stepped inner sidewalls, and which define a passage open at its bottom end to permit substantially unhindered fall of particulate matter therefrom, are also within the scope of the present invention.

While FIGS. 3 to 7 show a probe having two fluid coolant channels 68a,68b, it is to be appreciated that a probe 40 having three, four or more separate coolant channels is also possible. Similarly, while the use of water is disclosed as a suitable coolant fluid, other coolant fluids, including glycol mixtures and the like could equally be used.

The preferred embodiments describe the invention with reference to an electric arc furnace 12, however, the present invention is equally suitable for use in sampling off-gases from all high temperature applications where particle filter degradation as a result of contact with high temperature gases remains a problem.

Although the disclosure describes and illustrates preferred embodiments of the invention, the invention is not so limited. Many modifications and variations will now occur to persons skilled in the art. For a definition of the invention, reference may be had to the appended claims.

We claim:

1. An apparatus for sampling high temperature furnace off-gases from an off-gas stream and for delivering sample gas substantially free of particulate matter to gas analyzer means, the apparatus including, an elongated sampling probe, gas conduit means providing gaseous communication between said probe and said gas analyzer means and means for vacuum drawing said sample gas to said gas analyzer via said conduit means, the sampling probe including, an inner sidewall substantially defining an elongated, vertically extending substantially cylindrical sample gas passage, said passage open to the stream at a lowermost open end, an upper opening spaced above said open end and permitting gas flow between said passage and said conduit means, an outer sidewall spaced radially outwardly about at least part of said inner sidewall and defining a generally annular chamber therebetween, upper chamber wall means extending radially from said inner sidewall to said outer sidewall, lower chamber wall means extending radially from said inner sidewall to said outer sidewall and closing a lowermost end of the annular chamber, first and second partition means, each extending across said annular chamber between said inner sidewall and said outer sidewall, and being spaced from said lower wall means to divide the annular chamber into at least two fluid communicating coolant fluid channels for cooling said sample gas in said passage, means for introducing coolant fluid into said coolant fluid channels, filter means disposed in said cylindrical sample gas passage said filter means provided across said upper opening for filtering particulate matter from said sample gas as said sample gas is drawn through said upper opening, the lowermost open end substantially unobstructing downward movement of said particulate matter filtered from said sample gas, outwardly from said gas passage.

2. An apparatus as claimed in claim 1, wherein filter means comprises a porous silicon carbide filter.

3. An apparatus as claimed in claim 2, wherein said cylindrical sidewall is centred about a vertical axis, said upper opening is provided through a top portion of said probe centred on said axis, and said silicon carbide filter is an elongated filter extending axially downwardly from said upper opening a distance of between about 3 and 12 inches, and said filter includes coupling means for releasbly coupling said filter in said upper opening.

4. An apparatus as claimed in claim 1, wherein said upper opening is provided through a top portion of said probe, and comprises a threaded opening formed through said top portion, and said filter means includes threaded coupling means for releasably threadedly coupling said filter means in said threaded opening.

5. An apparatus as claimed in claim 1, wherein said probe further includes vent port means for venting backflow gas directly into said gas passage, said vent port means spaced towards said upper opening, and said apparatus further includes a source of backflow gas at a pressure above pressure of said off-gas stream, and valve means selectively operable to connect said conduit means to one of:

said vacuum means, wherein said gas sample is drawn upwardly along said passage from said off-gas stream and through said conduit means to the gas analyzer via the upper opening, and said source of backflow gas, whereby said conduit means permits backflow gas to backflow through at least one of the filter means via said upper opening and downwardly in said passage to dislodge particulate matter retained on said filter means, and the vent port means to back flow downwardly in said passage and dislodge particulate matter retained on said inner sidewall.

6. An apparatus as claimed in claim 5, wherein said backflow gas comprises a substantially non-reactive gas selected from the group consisting of nitrogen, argon, neon, xenon and helium.

7. An apparatus as claimed in claim 1, wherein said filter means comprises a filter body which includes, a hollow perforated sleeve support sized for fitted insertion through said upper opening, a high temperature fibre filter sleeve sized for placement over said sleeve support, and retaining means for retaining said filter sleeve substantially over said sleeve support.

8. An apparatus as claimed in claim 7 wherein said sleeve is expandable to an at least partially inflated configuration during backflow purging of the filter body.

9. An apparatus for obtaining a high temperature gas sample from an electric arc furnace off-gas stream and for delivering said sample to a gas analyzer, the apparatus comprising, a hollow sampling probe defining a vertically oriented elongated cylindrical sample gas passage, said passage opening downwardly at its lowermost end into a bottom opening of said off-gas stream, said probe including an upper opening through which said sample gas moves from said gas passage to the gas analyzer, vacuum means in gaseous communication with said upper opening for drawing said sample from said off-gas stream into said passage via said bottom end opening and outwardly from said passage through said upper opening to said gas analyzer, filter means disposed in said cylindrical sample gas passage said filter means provided across said upper opening for filtering particulate matter from said sample as said sample is drawn through said upper opening, vent port means for venting backflow gas directly into said gas passage said vent port means spaced towards said upper opening and backflow gas supply means selectively operable to supply backflow gas to said passage through said vent port means and through the filter means via the upper opening, whereby said backflow gas supplied to said passage flows downwardly along said passage to dislodge particulate matter retained on said inner sidewall.

10. An apparatus as claimed in claim 9, wherein said filter means comprises a filter body which includes, a hollow perforated sleeve support sized for fitted insertion through said upper opening, a high temperature fibre filter sleeve sized for placement over said sleeve support, and retaining means for retaining said filter sleeve substantially over said sleeve support.

11. An apparatus as claimed in claim 9, wherein said upper opening is provided through a top portion of said probe, said upper opening comprises a threaded opening formed through said top portion, and said filter means includes threaded coupling means for releasably threadedly coupling said filter means in said threaded opening.

12. An apparatus as claimed in claim 9 wherein said backflow gas supply means is operable to independently supply said backflow gas to said vent port means and through said filter means.

13. An apparatus as claimed in claim 9, wherein said tube further comprises an inner sidewall substantially defining said cylindrical passage, an outer sidewall spaced radially outwardly about at least part of said inner sidewall and defining a generally annular chamber therebetween, upper and lower wall means, each extending radially from said inner sidewall to said outer sidewall, said upper and lower wall means closing a respective upper and lower end portion of said annular chamber, first and second partition means, each extending across said annular chamber between said inner sidewall and side outer sidewall, and being spaced from said lower wall means to divide the annular chamber into at least two fluid communicating coolant fluid channels for cooling said sample gas in said passage, and means for introducing coolant fluid into said coolant fluid channels.

14. An apparatus as claimed in claim 13, wherein said bottom opening has a radial diameter equal to that of said gas passage so as to permit substantially unhindered movement of said particulate matter downwardly from said passage.

15. An apparatus as claimed in claim 14, wherein said backflow gas supply means comprises a source of gas at a pressure above pressure in said passage, said apparatus further including conduit means providing selective gaseous communication between the upper opening and said vacuum means, and conduit valve means operable to selectively connect the upper opening to either:
(a) said vacuum means, whereby said vacuum means draws gas outwardly from said passage through said filter means via said upper opening, or
(b) said source of gas, whereby the conduit means permits gas from the source of gas to backflow into the passage and through at least one of the filter means via the upper opening and the vent port means.

16. Use of an apparatus for sampling and analyzing high temperature furnace off-gases from an off-gas stream and for controlling furnace operations in response to the sample analysis, the apparatus comprising, gas analyzer means for analyzing said sample gas, an elongated sampling probe, and gas conduit means providing gaseous communication between said probe and said gas analyzer means and vacuum means for drawing said sample gas to said gas analyzer via said conduit means, the sampling probe comprising, an inner sidewall substantially defining an elongated substantially cylindrical sample gas passage, said passage open to the stream at a lowermost open end, an upper opening spaced above said open end and permitting gas flow between said passage and said conduit means, an outer sidewall spaced radially outwardly about at least part of said inner sidewall and defining a generally annular chamber therebetween, upper chamber wall means extending radially from said inner sidewall to said outer sidewall, lower chamber wall means extending radially from said inner sidewall to said outer sidewall and sealing a lowermost end of the annular chamber, first and second partition means, each extending across said annular chamber between said inner sidewall and said outer sidewall, and being spaced from said lower wall means to divide the annular chamber into at least two fluid communicating coolant fluid channels for cooling said sample gas in said passage, means for introducing coolant fluid into said coolant fluid channels, filter means disposed in said cylindrical sample gas passage, said filter means provided across said upper opening for filtering particulate matter from said sample gas as said sample gas is drawn through said upper opening, wherein the lowermost open end substantially unobstructs downward movement of said particulate matter filtered from said sample gas, outwardly from said gas passage, and backflow gas supply means selectively operable to supply backflow gas flow downwardly along said gas passage, wherein while said gas passage is in a substantially vertical orientation sampling of said off-gas is performed by the steps of:

(a) activating said vacuum means for drawing a sample to said gas analyzer via said gas passage to draw an off-gas sample into said gas passage via the lowermost open end, (b) simultaneously while drawing said sample, circulating coolant fluid through said coolant channels to cool said sample as its moves along the passage, and (c) periodically interrupting the drawing of said off-gas sample and activating said backflow gas supply means to provide backflow gas along said gas passage to assist in dislodging particulate matter therein.

17. Use of an apparatus as claimed in claim 16, wherein said apparatus further includes furnace control means in electronic communication with said gas analyzer means, said furnace control means including furnace control signal output means for outputting furnace controlling signals and data storage means, said method including the further steps of:

(d) storing first data representative of at least one furnace heat in said data storage means, (e) comparing sample data from said gas sample to said first data; and (f) outputting said signals from said furnace control signal output means to adjust furnace operations in response to said comparing step.

18. Use of an apparatus as claimed in claim 17, wherein said first data comprises a normalized heat profile.

19. Use of an apparatus as claimed in claim 16, wherein said coolant fluid is pumped through the coolant channels at a rate of between about 40 to 80 gallons per minute.

20. Use of an apparatus as claimed in claim 16, wherein said backflow gas comprises a substantially non-reactive gas selected from the group consisting of nitrogen, helium, neon, xenon and argon.

21. Use of an apparatus as claimed in claim 16, wherein said probe further includes vent port means for venting said backflow gas directly into said gas passage, said vent port means spaced towards said upper opening, and valve means selectively operable to connect said conduit means to one of:

said vacuum means, wherein said gas sample is drawn upwardly along said passage from said off-gas stream and through said conduit means to the gas analyzer via the upper opening, and said source of backflow gas, whereby said conduit means permits backflow gas to backflow downwardly in said pass age through at least one of the filter means via said upper opening and the vent port means.

* * * * *